United States Patent [19]

Bertolini

[11] Patent Number: 4,794,104

[45] Date of Patent: Dec. 27, 1988

[54] PHARMACEUTICAL COMPOSITIONS CONTAINING ACTH FRAGMENTS FOR THE THERAPY OF SHOCK CONDITIONS AND OF RESPIRATORY AND CARDIOCIRCULATORY INSUFFICIENCIES

[76] Inventor: Alfio Bertolini, 8, Vittorio Veneto Street, Scandiano, Italy

[21] Appl. No.: 183

[22] Filed: Jan. 2, 1987

[30] Foreign Application Priority Data

Jan. 15, 1986 [IT] Italy ............... 19086 A/86

[51] Int. Cl.$^4$ ............................................. A61K 37/40
[52] U.S. Cl. ...................................................... 514/13
[58] Field of Search .................... 530/306, 312; 514/13

[56] References Cited

U.S. PATENT DOCUMENTS

| | | | |
|---|---|---|---|
| 3,228,926 | 1/1966 | Kappeler et al. | 530/306 |
| 3,234,201 | 2/1966 | Schwyzer et al. | 530/312 |
| 3,247,182 | 4/1966 | Schwyzer et al. | 530/306 |
| 3,264,280 | 8/1966 | Hofmann et al. | 530/306 |
| 3,345,354 | 10/1967 | Kappeler et al. | 530/306 |
| 3,352,844 | 11/1967 | Boissonnas et al. | 530/306 |
| 3,388,112 | 6/1968 | Geiger et al. | 530/306 |
| 3,479,333 | 11/1969 | Greven | 530/306 |
| 3,483,291 | 12/1969 | Vogel et al. | 530/306 |
| 3,632,743 | 1/1972 | Geller et al. | 530/306 |
| 3,639,383 | 2/1972 | Geller | 530/306 |
| 3,678,027 | 7/1972 | De Jager et al. | 530/306 |
| 3,749,704 | 7/1973 | Geiger et al. | 530/306 |
| 3,810,880 | 5/1974 | Medzihradszky et al. | 530/306 |
| 3,862,111 | 1/1975 | Low et al. | 530/306 |
| 3,873,510 | 3/1975 | Kisfaludy et al. | 530/306 |
| 3,915,949 | 10/1975 | Colescott et al. | 530/306 |
| 4,457,864 | 7/1984 | Hruby et al. | 530/312 |

OTHER PUBLICATIONS

Chem. Abstr., vol. 105 (1986), 219256.
Chem. Abstr., vol. 104 (1986), 123443.
Chem. Abstr., vol. 102 (1985), 125730.
Chem. Abstr., vol. 101 (1984), 204630.
Chem. Abstr., vol. 99 (1983), 134114.
Chem. Abstr., vol. 92 (1980), 16006.
Chem. Abstr., vol. 87 (1977), 146131.
Chem. Abstr., vol. 84 (1976), 503.
Chem. Abstr., vol. 107 (1987), 52366.

*Primary Examiner*—Delbert R. Phillips
*Attorney, Agent, or Firm*—Walter H. Schneider

[57] ABSTRACT

The parenteral administration of 80–160 μg per kg body weight of substituted or unsubstituted fragments of ACTH (1–39) having formula ACTH (X–Y) wherein X is an integer from 1 to 5 and Y is an integer from 10 to 39 (provided that, when X is 1, Y is not 24) restores the normal blood pressure and respiratory frequence in a patient in serious shock conditions, particularly in hypovolemic shock.

4 Claims, 1 Drawing Sheet

PHARMACEUTICAL COMPOSITIONS CONTAINING ACTH FRAGMENTS FOR THE THERAPY OF SHOCK CONDITIONS AND OF RESPIRATORY AND CARDIOCIRCULATORY INSUFFICIENCIES

The present invention refers to pharmaceutical compositions for the treatment of shock conditions and of respiratory and cardiocirculatory insufficiencies, characterized by comprising, as the active principle, a polypeptide selected from the group consisting of (a) a fragment of ACTH (1-39) having formula ACTH (X-Y) wherein: X is an integer from 1 to 5 and Y is an integer from 10 to 39, provided that, when X is 1, Y is different from 24;

(b) the N-acetyl and N,O-diacetyl derivatives of said ACTH fragment (X-Y); and (c) 4-norleucine, 7-D-phenylalanine-α-MSH; and a pharmaceutically acceptable excipient.

Preferably, according to the invention, the ACTH fragments are sequences not higher than ACTH (1-24) and different from the sequence of ACTH (1-24), because the use of ACTH (1-24) for the therapeutic treatment of shock conditions, of respiratory and cardiocirculatory insufficiencies has been already described in the European Patent Application No. 86201461.0, in the Applicant's name.

Nevertheless, while the previous therapeutic uses of ACTH (1-24), concerning the treatment of insufficient response of the adrenal gland to the ACTH administration by intramuscular route and as a co-adjuvant in onchology, were already known, for the ACTH fragments (a), (b) and (c), according to the invention, no previous therapeutic use is known.

As is well-known, shock is a clinical condition essentially characterized by an insufficient tissue perfusion, with usually serious hypotension which, if not treated, is generally fatal. Shock may be caused by different causes, such as serious hemorrhages, cranial trauma, dangerous cardiac insufficiency as in certain myocardial infarcts, anaphylactic reactions, etc.

The therapy used at the present time, which is not suited for all kinds of shock, turns out to be unsatisfactory.

Generally, in all shock conditions, there is a tendency to restore the blood volume by means of blood, plasma, saline or glucose solutions or plasma substituents infusion; or to administer oxygen.

However, in serious shock conditions, said treatment is usually insufficient if not even counteracting. In fact, in the cardiogenic shock, infusion of liquids will overload the heart, whose function is already seriously impaired because of the insufficient myocardial contractility.

Administration of vasoconstrictor drugs, such as noradrenaline, adrenaline, metaraminol, mephentermine, in order to increase pressure, often causes the opposite effect, since, under shock conditions (with the exclusion of the neurogenic shock) a severe sympathetic reflex vasoconstriction is already present, whereby tissular perfusion would be further impaired.

On the contrary, administration of drugs such as dopamine, dobutamine, isoproterenol, glucagon, etc. which improve cardiac inotropism without substantially increasing the peripheral resistances, is preferred, particularly in case of cardiogenic shock.

On the other hand, in some instances, administration of vasodilating drugs such as nitroprussiate and α-blockers may be convenient, in order to improve tissue perfusion.

Notwithstanding corticosteroids are widely used in the treatment of shock, no convincing proofs are available supporting the effectiveness of said drugs.

Recently, the efficacy of naloxone in different models of shock has been also studied. Although naloxone turned out to be effective in restoring normal blood pressure values, it is absolutely contraindicated in the shock due to overdose. It is in fact known that naloxone administration to narcotic addicted subjects is followed by a typical abstinence syndrome. Moreover, naloxone at the dosages therapeutically active in shock (about 1 mg/kg) provokes hyperalgesia and may induce serious side-effects such as ventricular fibrillation and pulmonary oedema.

Now it has been surprisingly found that the use of ACTH fragments (a), (b) and (c) is dramatically effective in the therapeutic treatment of shock (hypovolemic, cardiogenic, traumatic, toxic and anaphylactic shocks), cardiovascular collapse, acute hypotension and respiratory insufficiency, independently from the graumatic, psychogenic, toxic, drug overdose causes etc. The preferred fragments according to this invention will exclude from the molecular portion of the "tail" sequence of ACTH the sequence (25-39).

Fragments of ACTH lower than ACTH (1-24) which turned out to be particularly suited for the preparation of pharmaceutical compositions for the therapeutic treatment of shock, cardiovascular collapse, acute hypotension and respiratory insufficiency are: ACTH (4-10), ACTH (1-13), ACTH (1-16), ACTH (1-17), ACTH (1-18), ACTH (5-13) and N-acetyl and N,O-diacetyl derivatives thereof.

For instance, in the hypovolemic shock, which is always fatal when the blood loss exceeds 50% of the total blood volume, said ACTH fragments are able to restore to the normal values cardiac output, arterial pressure and breath frequency and amplitude. This effect starts to appear already a few minutes after intravenous injection, it reaches the maximum within 15-20 minutes, it is dose-dependent and require no simultaneous infusion of blood or plasma substitutes.

Even when used as analeptic, said ACTH fragments show remarkable advantages in comparison with known analeptics. In fact, all the up to now available analeptics are convulsivant agents used at sub-convulsive dosages, and therefore with a very low therapeutic index and poor handling characteristics; moreover, said ACTH fragments normalize the circulatory and respiratory functions if they are depressed, without changing them when they are normal.

While ACTH (1-24) is substantially non-toxic, said ACTH fragments are completely non-toxic and devoid of any side-effect, in particular adrenal-like or allergizing activity.

Administration of the ACTH fragments will be preferably carried out by the intravenous route in the shock conditions and by nasal inhalation when the ACTH fragments are used as analeptics.

In any case, it has been found that the therapeutically effective dose is comprised from about 80 to about 160 μg of ACTH fragment per kg body weight.

Thus, a suitable pharmaceutical composition to be adminstered parenterally, in form of a unit dosage, will comprise from about 1 to about 10 mg of said ACTH fragments and a pharmacologically acceptable excipient.

The above mentioned composition will be generally extemporaneously prepared by the physician or by the patient. The commercially available pharmaceutical form will be therefore a preparation in unit dosage form comprising a vial containing from about 1 to about 10 mg of ACTH fragments and a vial containing a pharmaceutically acceptable solvent for said ACTH fragments.

When used as an analeptic for the treatment of respiratory and cardiocirculatory insufficiencies the pharmaceutical composition according to the invention will be in an appropriate form for administration by the inhalatory route, for example as a nasal spray, and it will therefore comprise a therapeutically effective amount of a ACTH fragment and a gaseous or vaporizable pharmaceutically acceptable excipient. The choice of the most suitable excipients is within the skilled in the art's reach.

The effectiveness of ACTH fragments in the treatment of shock has been confirmed by several tests on animals and by clinical studies. Some of said tests and the obtained results are reported hereinafter.

TESTS ON EXPERIMENTAL ANIMALS

Intact and adrenalectomized female Wistar rats (Nossan, Correzzano, Milano, Italy) weighing 250 to 300 g, were used. Following anesthetization and heparinization a common carotid artery and an iliac vein were cannulated in rats. Arterial blood pressure was recorded by means of a pressure transducer (Statham P23 Db) connected to a polygraph (Battaglia-Rangoni, Bologna, Italy). In some rats, trachea was cannulated and respiration was recorded by means of a transducer (Statham 10272) connected to the same polygraph. Hypovolemic shock was produced by intermittently withdrawing blood from the venous catheter until mean arterial pressure fell to 16-30 mm Hg. The volume of blood removed was 2-2.5 ml per 100 g of body weight and approximated to, or even exceeded, 50% of the estimated total blood volume. Following bleeding and mean blood pressure stabilization in the range of 16-30 mm Hg, animals were given intravenous bolus of either ACTH fragments. Control animals were intravenously injected with the same volume of saline (0.1 ml/100 g of body weight).

In FIGS. 1-3 some representative recordings are reported, while the Table shows the data from some tests.

From the examination of the recordings and data it is evident that the intravenous injection of ACTH fragments dose-dependently restores blood pressure and pulse amplitude, the effect starting within a few minutes, gradually increasing, and reaching a maximum in 15-30 minutes. All rats intravenously injected with the same volume of saline died after about 18-22 minutes.

The results from this study demonstrate that the ACTH fragments increase blood pressure and reverse otherwise fatal hypovolemic shock resulting from massive bleeding, in rats and dogs. This effect is not mediated by adrenals, because it is neither abolished nor reduced by adrenalectomy.

Although it is not intended to rely on any theoretical interpretation to explain the therapeutic effectiveness of the ACTH fragments in the applications of the present invention, the obtained results, showing that said ACTH fragments are even more active than naloxone in reversing shock, and that their action is very probably at the CNS level, are consistent with the hypothesis that melanocortins are endovenous antagonists of opioids, and give further experimental support to the suggested existence of a melanocortin-opioid peptidergic system, with a wide functional meaning and with homeostatic, regulatory roles in many, important functions of the body.

In the light of the present results, the hypothesis that shock, rather than the consequence of a massive activation of endogenous opioid system, is the final effect of the melanocortin-opioid homeostasis with prevalence of the opioid component, should be formulated.

With reference to the diagrams illustrated in the drawings.

TABLE 1

Figure 1:
FIG. 1 shows the effect of a saline solution (s), 0.1 ml/100 g body weight, on the blood pressure after serious hypotension induced by bleeding in the rat.
Figure 2:
FIG. 2 shows the effect of ATCH (4-10), (c) 160 μg/kg i.v. on the blood pressure after serious hypotension induced by bleeding in the rat.
Figure 3:
FIG. 3 shows the effect of ACTH (1-16), (c), 160 μg/rat i.v. on the blood pressure after serious hypotension induced by bleeding in the intact rat.

Effect of ACTH fragments and saline treatment on mean arterial pressure and survival in animals affected by severe hypotension induced by bleeding

| ANIMALS* | TREATMENT AFTER BLEEDING (μg/kg i.v.) | MEAN ARTERIAL PRESSURE (mm Hg; m ± S.E.) | | | No. of deaths 120 min. after treatment |
|---|---|---|---|---|---|
| | | Before bleeding | After bleeding | 15-30 min. after treatment | |
| Rats (12) | Saline i.v. | 72.43 ± 8.60 | 17.50 ± 4.36● | 18.25 ± 3.91 | 12 |
| Rats (10) | ACTH-(1-24), 160 | 82.40 ± 10.75 | 23.15 ± 2.90● | 75.80 ± 8.45▲ | 0 |
| Rats (8) | ACTH-(1-24), 80 | 80.15 ± 9.43 | 19.23 ± 3.65● | 59.48 ± 8.10▲ | 0 |
| Rats (6) | ACTH-(1-24), 40 | 82.33 ± 11.73 | 17.40 ± 2.68● | 39.40 ± 6.32▲ | 0 |
| Rats (6) | ACTH-(1-39), 160 | 88.25 ± 2.17 | 14.75 ± 2.32● | 35.75 ± 5.65▲ | 0 |
| Rats (6) | ACTH(25-39), 160 | 78.17 ± 7.25 | 11.50 ± 1.34● | 25.50 ± 4.40■ | -1 |
| Rats (6) | ACTH-(1-18), 160 | 53.00 ± 4.88 | 15.00 ± 2.12● | 38.50 ± 1.85▲ | 0 |
| Rats (6) | ACTH-(1-17), 160 | 57.50 ± 7.17 | 15.75 ± 2.29● | 41.50 ± 3.75▲ | 0 |
| Rats (6) | ACTH-(1-16), 160 | 78.25 ± 12.46 | 15.50 ± 2.53● | 54.50 ± 2.02▲ | 0 |
| Rats (6) | ACTH-(1-13), 160 | 66.25 ± 9.14 | 15.75 ± 1.31● | 34.50 ± 1.32▲ | 0 |
| Rats (6) | ACTH-(4-10), 160 | 63.25 ± 6.76 | 13.75 ± 2.53● | 47.25 ± 6.18▲ | 0 |

*In parentheses the number of animals used;
● $P < 0.02$, at least, versus value before bleeding;
▲ $P < 0.01$, at least, versus value after bleeding;
■ $P < 0.05$, at least, versus value after bleeding (Student's t-test for paired data).

I claim:

1. A method of therapeutically treating a subject suffering from shock or respiratory or cardiocirculatory insufficiencies which comprises administering to said subject a composition comprising as the principal active ingredient a polypeptide selected from the group consisting of
   (a) a fragment of ACTH (1–39) having the formula ACTH (X–Y) wherein X is an integer from 1–5 and Y is an integer from 10–39, provided that when X is 1, Y is different from 24;
   (b) the N-acetyl and N,O-diacetyl derivatives of said ACTH fragment (X–Y); and
   (c) 4-norleucine, 7-D-phenylalanine-$\alpha$-MSH; in admixture with a pharmaceutically acceptable excipient.

2. A method according to claim 1 in which said composition is adapted for parenteral administration and comprises about 1.0–10 mg of said polypeptide.

3. A method according to claim 1 in which said composition is adapted for inhalatory administration in the treatment of respiratory and cardiovascular insuffciencies and comprises an effective amount of said polypeptide in admixture with a pharmaceutically acceptable gaseous or vaporizable excipient.

4. A method according to claim 2 in which said composition is in the form of a kit comprising a vial of said polypeptide and a vial of a pharmaceutically acceptable solvent for said polypeptide.

* * * * *